United States Patent
Harmouche et al.

(10) Patent No.: US 9,522,030 B2
(45) Date of Patent: Dec. 20, 2016

(54) PURGE PHASE FOR CRYOABLATION SYSTEMS

(71) Applicant: MEDTRONIC CRYOCATH LP, Toronto (CA)

(72) Inventors: Chadi Harmouche, St-Laurent (CA); Rachid Mahrouche, Lasalle (CA); Eric Monger, Beloeil (CA); Bertin Siméon, Laval (CA); Vladimir Tzonev, Kirkland (CA)

(73) Assignee: Medtronic CryoCath LP, Toronto, Ontario (CA)

( * ) Notice: Subject to any disclaimer, the term of this patent is extended or adjusted under 35 U.S.C. 154(b) by 181 days.

(21) Appl. No.: 13/747,902

(22) Filed: Jan. 23, 2013

(65) Prior Publication Data
US 2014/0207131 A1    Jul. 24, 2014

(51) Int. Cl.
*A61B 18/18*    (2006.01)
*A61B 18/02*    (2006.01)

(52) U.S. Cl.
CPC ........ *A61B 18/02* (2013.01); *A61B 2018/0212* (2013.01); *A61B 2018/0262* (2013.01)

(58) Field of Classification Search
CPC .............. A61B 18/02; A61B 208/0212; A61B 208/0262
USPC ..................................................... 606/20–26
See application file for complete search history.

(56) References Cited

U.S. PATENT DOCUMENTS

| | | | |
|---|---|---|---|
| 3,398,738 A | 8/1968 | Lamb et al. | |
| 4,018,227 A | 4/1977 | Wallach | |
| 5,388,415 A | 2/1995 | Glinka et al. | |
| 5,758,505 A * | 6/1998 | Dobak, III et al. | .... A61B 18/02 606/23 |
| 6,355,029 B1 * | 3/2002 | Joye | ........................ A61B 18/02 606/21 |

(Continued)

FOREIGN PATENT DOCUMENTS

| | | |
|---|---|---|
| EP | 0955012 A1 | 11/1999 |
| WO | 9067226 A1 | 6/1990 |

OTHER PUBLICATIONS

International Search Report and Written Opinion dated Mar. 27, 2014 for International Application Serial No. PCT/CA2013/001055, International Filing Date: Dec. 17, 2013 consisting of 8 pages.

(Continued)

*Primary Examiner* — Michael Peffley
*Assistant Examiner* — Amanda Zink
(74) *Attorney, Agent, or Firm* — Christopher & Weisberg, P.A.

(57) ABSTRACT

A method for purging a cryotreatment system, in particular, for clearing moisture and thus preventing ice blockages within a fluid flow path that may be formed when moisture pockets within the fluid flow path of the system are encountered by a first injection of refrigerant at the beginning of a cryotreatment procedure. The method may include injecting refrigerant from a refrigerant source into a fluid delivery conduit at a preselected pressure for a first period of time, the refrigerant flowing from the fluid delivery conduit through a fluid injection element and into a fluid recovery conduit, and evacuating refrigerant from the fluid recovery conduit by vacuum pressure generated by the vacuum pump for a second period of time. This method may be repeated for a plurality of cycles.

18 Claims, 4 Drawing Sheets

(56) References Cited

U.S. PATENT DOCUMENTS

| | | | | |
|---|---|---|---|---|
| 6,471,694 B1* | 10/2002 | Kudaravalli | ............... | F25D 3/10 |
| | | | | 606/21 |
| 6,635,053 B1* | 10/2003 | Lalonde | ................. | A61B 18/02 |
| | | | | 606/22 |
| 6,648,879 B2* | 11/2003 | Joye | ........................ | A61B 18/02 |
| | | | | 128/898 |
| 6,991,630 B2* | 1/2006 | Ryba | ........................ | A61B 18/02 |
| | | | | 606/20 |
| 7,207,986 B2* | 4/2007 | Abboud | ................. | A61B 18/02 |
| | | | | 606/20 |
| 2002/0045894 A1* | 4/2002 | Joye | ........................ | A61B 18/02 |
| | | | | 606/21 |
| 2002/0068929 A1* | 6/2002 | Zvuloni | ................. | A61B 18/02 |
| | | | | 606/22 |
| 2006/0004349 A1 | 1/2006 | Ryba et al. | | |
| 2008/0119834 A1 | 5/2008 | Vancelette et al. | | |
| 2011/0092967 A1* | 4/2011 | Harvey-Poncelet | ... | A61B 18/02 |
| | | | | 606/21 |
| 2012/0245574 A1 | 9/2012 | Lalonde | | |

OTHER PUBLICATIONS

Supplementary European Search Report dated Oct. 12, 2016, for corresponding European Application No. EP 13872804.3; European Filing Date: Aug. 5, 2015 consisting of 11-pages.

\* cited by examiner

PURGE PHASE FOR CRYOABLATION SYSTEMS

CROSS-REFERENCE TO RELATED APPLICATION n/a

STATEMENT REGARDING FEDERALLY SPONSORED RESEARCH OR DEVELOPMENT n/a

FIELD OF THE INVENTION

The present invention relates to a method and system for purging refrigerant pathways of moisture immediately prior to cardiac procedures.

BACKGROUND OF THE INVENTION

Cryoablation systems are frequently used for treating tissue in a cardiac setting, either to cool the tissue sufficiently to stun it and allow cold mapping of the heart and/or confirmation of catheter position with respect to localized tissue lesions. Additionally, such systems may be used to apply a more intense cold to ablate an area of target tissue, for example, tissue that has been identified as propagating an aberrant electric current in cases of cardiac arrhythmia.

In general, when used for endovascular access to treat the cardiac wall, cryoablation catheters must meet fairly demanding limitations regarding their size, flexibility, and the factors of strength, electrical conductivity and the like. These constraints generally require that the catheter be no larger than several millimeters in diameter so as to pass through the vascular system of the patient to the heart. Thus, any electrodes and refrigerant passages must fit within a catheter body of small size.

A number of different fluids have been used for the refrigerant component of prior art cryotreatment catheters, such as a concentrated saline solution or other liquid of suitably low freezing point and viscosity, and of suitably high thermal conductivity and heat capacity, or a liquified gas such as liquid nitrogen. In all such constructions, the refrigerant must circulate through the catheter, thus necessitating multiple passages leading to the cooling area of the tip from the catheter handle. In some systems, a phase change refrigerant is used that travels through the body of the catheter at a relatively normal or ambient temperature and attains cooling only upon expansion within a chamber at the tip region. In some systems, pressurized gas travels through the body of the catheter and into a spray nozzle in a cooling chamber at the tip region, where cooling is achieved by the Joule-Thomson effect when the gas expands. Due to the size limitations on the device as a whole, however, the outlet holes of the spray nozzle or other fluid injection outlets are necessarily very small. Consequently, the outlet holes easily become clogged or blocked, which may lead to failure at the beginning of a cardiac procedure.

One cause of blockage in the cryoablation system may be ice formation that occurs at the first fluid injection at the beginning of a cardiac procedure. Ambient humidity may creep into the system, for example, the refrigerant injection lumen, refrigerant recovery lumen, and/or injection apertures. This ambient humidity may create pockets of moisture within the system that rapidly become frozen when the refrigerant is first injected into the system at the beginning of a new cardiac procedure, creating ice blockages within the system. When this occurs, the system must be thawed and purged before the procedure may take place, and this delay may have disastrous effects. The small holes of an injection nozzle are particularly susceptible to retaining moisture and becoming blocked with ice.

Moisture pockets generated by ambient humidity within the system must be addressed immediately before a cardiac procedure. New moisture pockets may develop in a short period of time, and therefore may be present at the beginning of a procedure even if the system was purged within a few hours of the procedure. However, presently known purging processes are inefficient or take too long, thus also contributing to a delay in urgent cardiac procedures.

Accordingly, a cryoablation system purging process is desired that is efficient and effective, and can be performed quickly immediately prior to the beginning of a cardiac procedure.

SUMMARY OF THE INVENTION

The present invention advantageously provides a method and system for purging a cryotreatment flow path. In particular the method is for purging moisture and thus preventing ice blockages that may occur within a fluid flow path when moisture pockets within the fluid flow path of the system are encountered by a first injection of refrigerant at the beginning of a cryotreatment procedure. The method may generally include (a) providing a cryotreatment system including a refrigerant source, a fluid delivery conduit in fluid communication with the refrigerant source, a fluid injection element in fluid communication with the fluid delivery conduit, a fluid recovery conduit in fluid communication with the fluid injection element, and a vacuum pump in fluid communication with and providing a low pressure environment within the fluid recovery conduit, (b) injecting refrigerant from the refrigerant source into the fluid delivery conduit at a preselected pressure for a first period of time, the refrigerant flowing from the fluid delivery conduit through the fluid injection element and into the fluid recovery conduit, and (c) evacuating refrigerant from the fluid recovery conduit by vacuum pressure generated by the vacuum pump for a second period of time. Steps (b) and (c) may be performed a plurality of times (for example, each of Steps (b) and (c) may be performed four times. The first period of time is approximately 2 seconds and the second period of time is approximately 1 second. the predetermined pressure is between approximately 250 psi and approximately 350 psi, in particular, approximately 300 psi.

In one embodiment, the method may include (a) providing a cryotreatment system defining a fluid flow path including a fluid delivery conduit in fluid communication with a refrigerant source, a cryotreatment device having a balloon defining a lumen, a fluid injection element in fluid communication with the fluid delivery conduit and being disposed within the balloon lumen, a fluid recovery conduit in fluid communication with the balloon lumen, a vacuum pump in fluid communication with and providing a low pressure environment within the fluid flow path, and a compressor in fluid communication with the fluid recovery conduit and the fluid delivery conduit. The method may further include (b) injecting compressed refrigerant from the refrigerant source into the fluid delivery conduit at a pressure of between approximately 250 psi and approximately 350 psi for approximately two seconds, the compressed refrigerant flowing from the fluid delivery conduit through the fluid injection element and into the balloon lumen where the compressed refrigerant expands, the expanded refrigerant then flowing into the fluid recovery conduit, (c) evacuating the expanded refrigerant from the fluid recovery conduit into the fluid recovery conduit by low pressure generated by the vacuum pump for approximately one second, (d) directing the expanded refrigerant into the compressor and recompressing the expanded refrigerant, the compressor becoming the refrigerant source, and (e) repeating (b) and (c) for a plurality of additional cycles.

In another embodiment, the method may include (a) providing a cryotreatment system defining a fluid flow path including a refrigerant source, a fluid delivery conduit in fluid communication with the refrigerant source, a cryotreatment device having an elongate body, a balloon defining a lumen and a shaft having at least a portion disposed within the elongate body and at least a portion disposed within the balloon lumen, a fluid injection element in fluid communication with the fluid delivery conduit and being disposed about at least a portion of the shaft within the balloon lumen, a fluid recovery conduit in fluid communication with the balloon lumen, a fluid recovery reservoir in fluid communication with the fluid recovery conduit, and a vacuum pump in fluid communication with and providing a low pressure environment within the fluid recovery reservoir. The method may further include (b) injecting refrigerant from the refrigerant source into the fluid delivery conduit at a pressure of between approximately 250 psi and approximately 350 psi for approximately two seconds, the refrigerant flowing from the fluid delivery conduit through the fluid injection element, into the balloon lumen, and then into the fluid recovery conduit, evacuating refrigerant from the fluid recovery conduit into the fluid recovery reservoir by vacuum pressure generated by the vacuum pump for approximately one second, and repeating (b) and (c) for three additional cycles.

BRIEF DESCRIPTION OF THE DRAWINGS

A more complete understanding of the present invention, and the attendant advantages and features thereof, will be more readily understood by reference to the following detailed description when considered in conjunction with the accompanying drawings wherein.

DETAILED DESCRIPTION OF THE INVENTION

Figures 1A, 1B:
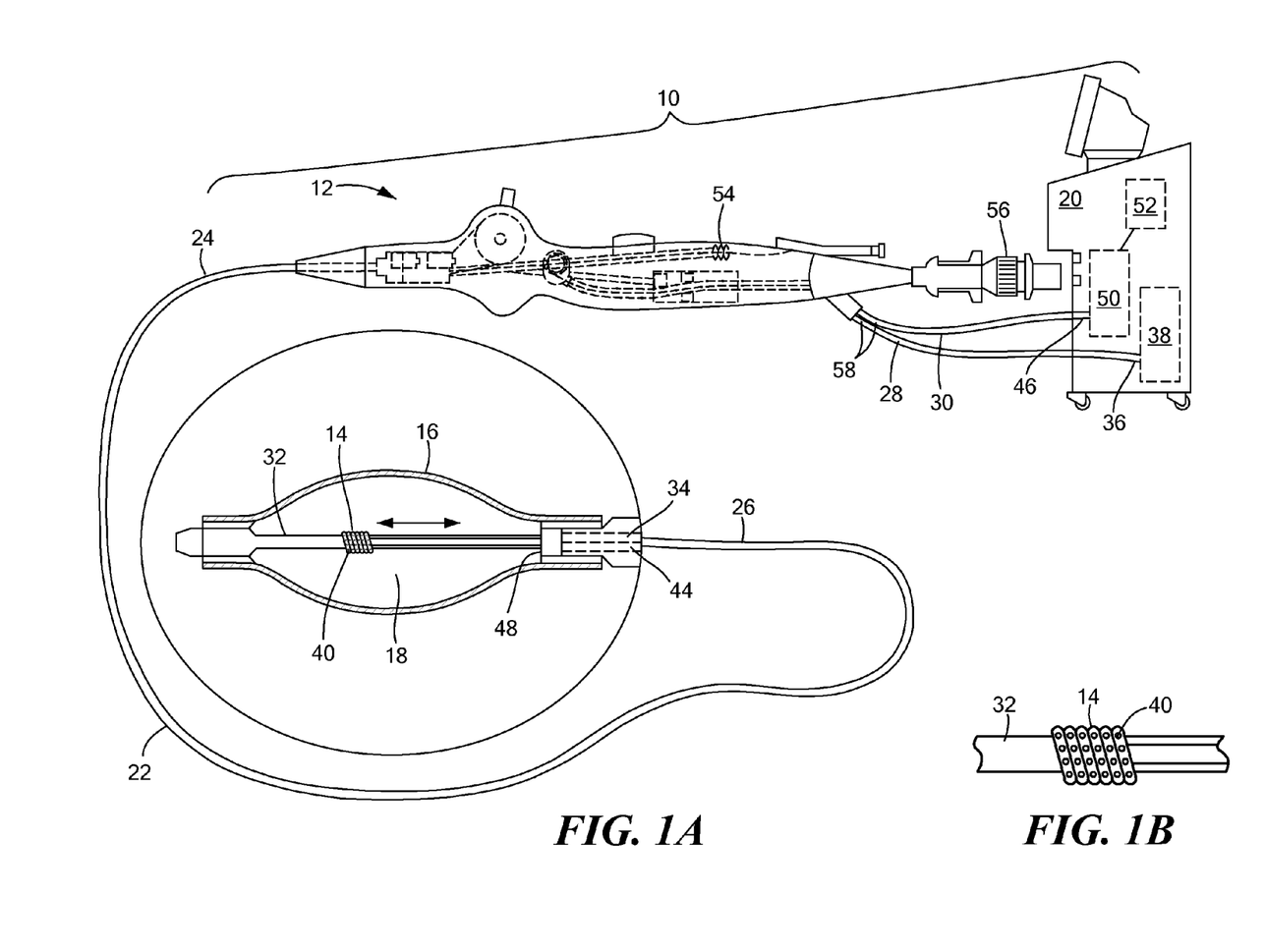
FIG. 1A shows a cryoablation system that may be purged using a method described herein.
FIG. 1B shows a close-up view of a fluid injection nozzle having a plurality of openings or apertures.
Figure 2:
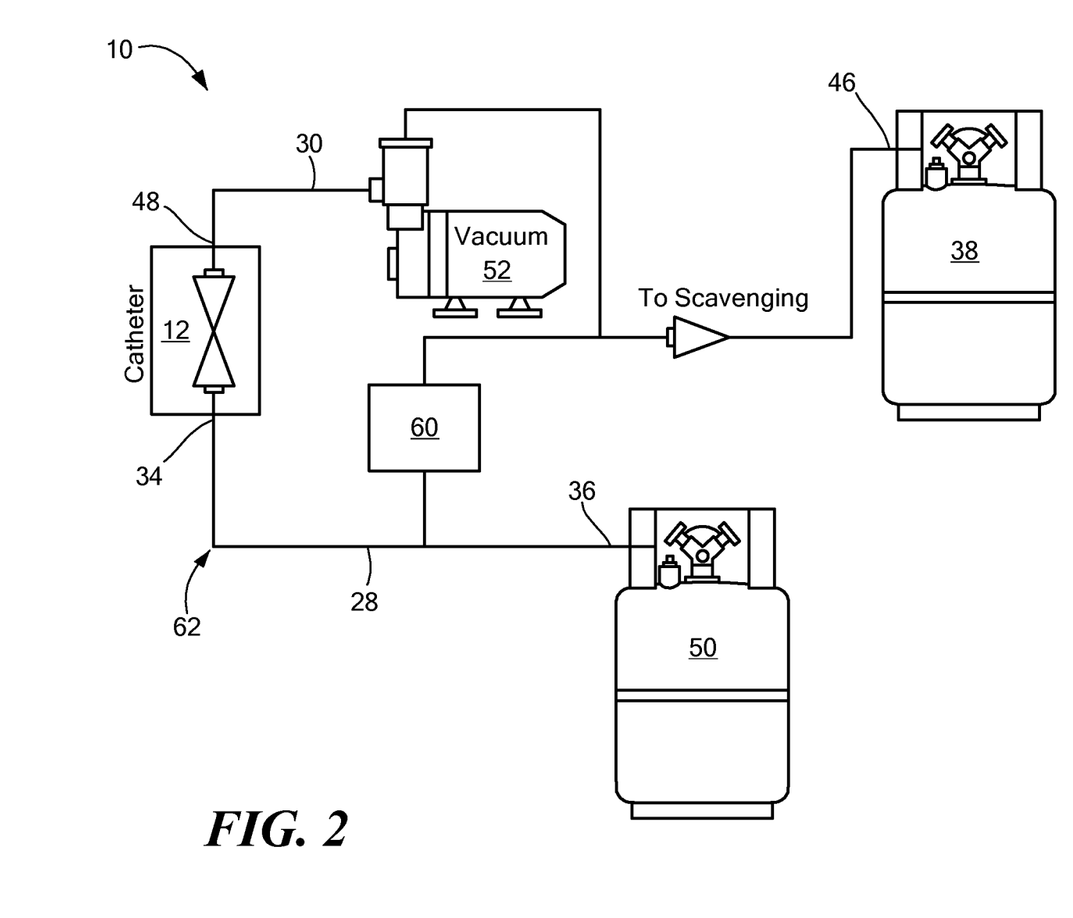
FIG. 2 shows a first embodiment of a fluid flow path of a cryoablation system.
Figure 3:
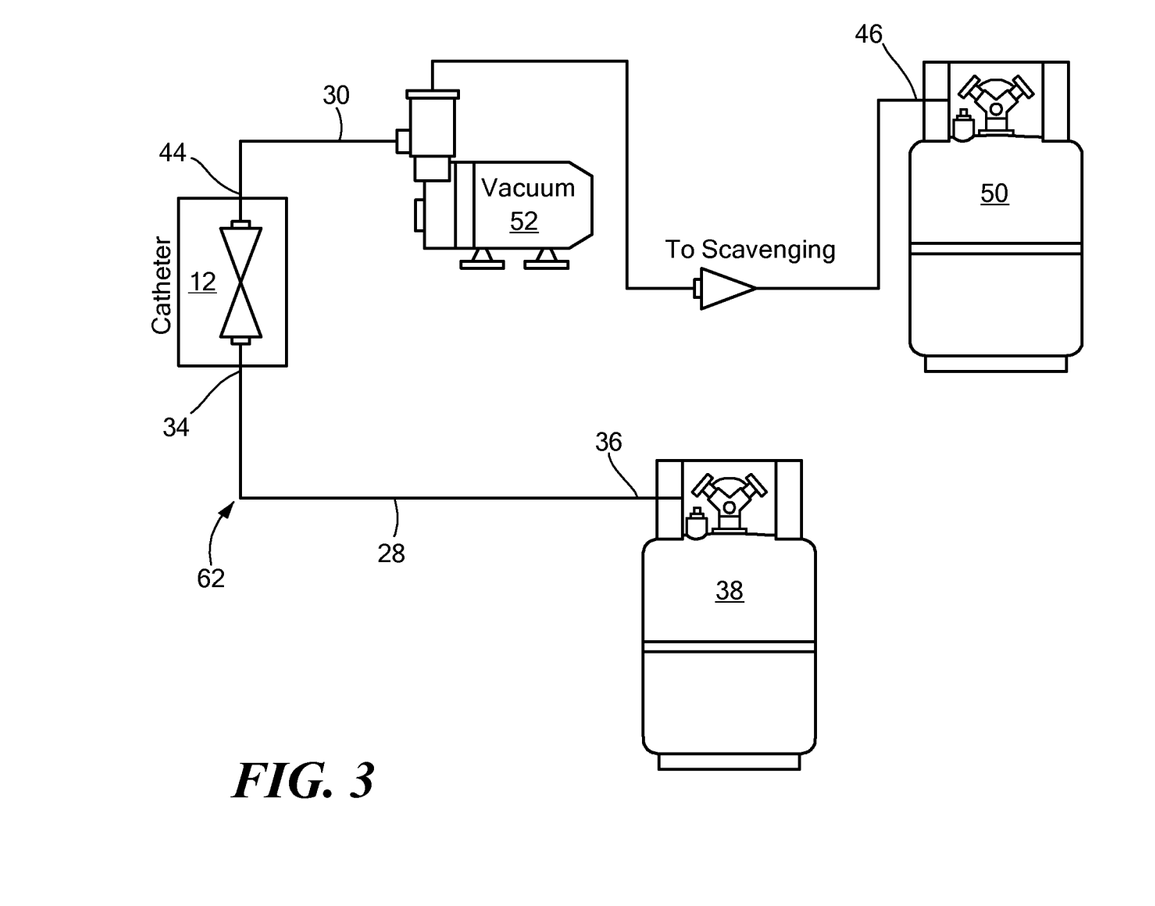
FIG. 3 shows a second embodiment of a fluid flow path of a cryoablation system.

Referring now to FIGS. 1-3, a cryoablation system 10 that may be purged using a method described herein is shown. The cryoablation system 10 may be used with any type of cryosurgical device 12 having a fluid injection means; however, a typical cryoballoon catheter having a fluid injection nozzle 14 in an expansion chamber is shown. The expansion chamber may be within an expandable element, such as a cryoballoon 16 and cryoballoon lumen 18, as shown in FIG. 1A. Alternatively, if a focal catheter is used that does not include an expandable element, the expansion chamber may be within a lumen within the catheter that is in thermal communication to a treatment element at, for example, the distal portion of the catheter. The system 10 generally includes a medical device 12 that may be coupled to a control unit or operating console 20. The medical device 12 may generally include one or more treatment regions, for example, one or more cryoballoons 16, for energetic or other therapeutic interaction between the medical device 12 and a treatment site. Although the system 10 described herein is used at least for cryogenic treatments, the system 10 may also be configured to deliver, for example, radiofrequency energy, microwave energy, ultrasound energy, or provide other energetic transfer with a tissue area in proximity to the treatment regions, including cardiac tissue.

The medical device 12 may include an elongate body 22 passable through a patient's vasculature and/or proximate to a tissue region for diagnosis or treatment, such as a catheter, sheath, or intravascular introducer. The elongate body 22 may define a proximal portion 24 and a distal portion 26, and may further include one or more conduits 28, 30 disposed within the elongate body 22 thereby providing fluid, mechanical, and/or electrical communication between the proximal portion 24 of the elongate body 22 and the distal portion 26 of the elongate body 22.

The medical device 12 may include a shaft 32 at least partially disposed within a portion of the elongate body 22. The shaft 32 may extend or otherwise protrude from a distal portion 26 of the elongate body 22 and into the lumen 18 of the cryoballoon 16, and may be movable with respect to the elongate body 22 in longitudinal and rotational directions. That is, the shaft 32 may be slidably and/or rotatably moveable with respect to the elongate body 22 (as depicted by the double-headed arrow in FIG. 1A). However, the movement of the shaft 32 may not have any impact on the purging process shown and described in FIG. 2.

The medical device 12 may further include a fluid delivery conduit 28 traversing at least a portion of the elongate body 22, from the proximal portion 24 to the distal portion 26. The fluid delivery conduit 28 may be coupled to or otherwise extend from the distal portion 26 of the elongate body 22, and may further be coupled to the shaft 32 of the medical device 12. For example, the fluid delivery conduit 28 may have a distal portion 34 and a proximal portion 36, and the distal portion 34 may be coiled or wound about a portion of the shaft 32 within the cryoballoon lumen 18, as shown in FIG. 1A and in greater detail in FIG. 1B. Alternatively, if a focal catheter is used, the fluid delivery conduit may be disposed within a lumen of the catheter. The fluid delivery conduit 28 may define a lumen therein for the passage or delivery of a fluid from the proximal portion 24 of the elongate body 22 and/or the console 20 to the distal portion and/or treatment region of the medical device 12. For example, the proximal portion 36 of the fluid delivery conduit 28 may be in fluid communication with a fluid reservoir or refrigerant source 38 and the distal portion 34 of the fluid delivery conduit 28 may be within the cryoballoon lumen 18 and include one or more apertures or openings 40 to provide for the dispersion or directed ejection of fluid from the fluid delivery conduit 28 to the cryoballoon lumen 18. These apertures or openings 40 may be particularly susceptible to ice blockages.

The medical device 12 may further include a fluid recovery conduit 30 traversing at least a portion of the elongate body 22, from the distal portion 26 to the proximal portion 24. The fluid recovery conduit 30 may define a distal portion 44, a proximal portion 46, and a lumen for the passage or delivery of a fluid from the distal portion 26 of the elongate body 22 to the proximal portion 24 of the elongate body 22. For example, the distal portion 44 of the fluid recovery conduit 30 may be in fluid communication with the cryoballoon lumen 18, from where expanded refrigerant may enter the fluid recovery conduit 30 through an opening or aperture 48 within the fluid recovery conduit 30. The proximal portion 46 of the fluid recovery conduit 30 may be in fluid communication with a fluid recovery reservoir 50 and vacuum pump 52.

The medical device 12 may include a handle 54 coupled to the proximal portion 24 of the elongate body 22. The handle 54 can include circuitry for identification and/or use in controlling of the medical device 12 or another component of the system 10. For example, the handle 54 may include one or more pressure sensors to monitor the fluid pressure within the medical device 12. The handle 54 may also include connectors 56 that are matable directly to the fluid reservoir 38, fluid recovery reservoir 50, and console 20 or indirectly by way of one or more umbilicals 58 (which may be part of the fluid delivery and recovery conduits). The handle 54 may further include blood detection circuitry in fluid and/or optical communication with the fluid delivery conduit 28 and fluid recovery conduit 30. The handle 54 may also include a pressure relief valve in fluid communication with the fluid delivery conduit 28 and/or fluid recovery conduit 30 to automatically open under a predetermined threshold value in the event that value is exceeded.

The system 10 may further include one or more sensors to monitor the operating parameters throughout the system 10, including for example, pressure, temperature, flow rates, volume, or the like in the console 20 and/or the medical device 12, in addition to monitoring, recording or otherwise conveying measurements or conditions within the medical device 12 or the ambient environment at the distal portion of the medical device 12. The one or more sensors may be in communication with the console 20 for initiating or triggering one or more alerts or therapeutic delivery modifications during operation of the medical device 12. One or more valves, controllers, or the like may be in communication with the one or more sensors to provide for the controlled dispersion or circulation of fluid through the fluid flow path (also referred to as a "fluid pathway") of the medical device 12. Such valves, controllers, or the like may be located in a portion of the medical device 12 and/or in the console 20.

The system 10 may further include one or more compressors and/or condensers, generally indicated as 60, to compress recovered expanded refrigerant for reuse during the purge process and/or cryosurgical procedure. In such an embodiment, such as is shown in FIG. 2, the fluid pathway 62 of the system 10 may be referred to as a closed loop configuration. Fluid may flow from the refrigerant source 38, into the fluid delivery conduit 28, into the fluid injection nozzle 14 (or other fluid injection element) into the expansion chamber (for example, a cryoballoon lumen 18, as shown in FIG. 1A), into the fluid recovery conduit 30, and through the one or more compressors and/or condensers 60, at which point the recovered refrigerant may be compressed and/or conditioned for reuse. Finally, the compressed and/or conditioned refrigerant may then flow back into the fluid delivery conduit 28. In an embodiment in which the recovered refrigerant is not reused, such as is shown in FIG. 3, the fluid pathway 62 of the system 10 may be referred to as an open-loop configuration. In this embodiment, fluid may flow from the refrigerant source 38, into the fluid delivery conduit 28, into the fluid injection nozzle 14 (or other fluid injection element) into the expansion chamber (for example, a cryoballoon lumen 18 as shown in FIG. 1A), into the fluid recovery conduit 30, and into the fluid recovery reservoir 50. The recovered refrigerant may then be discarded.

In an exemplary system, a fluid supply 60 including a coolant, cryogenic refrigerant, or the like, an exhaust or scavenging system for recovering or venting expended fluid for re-use or disposal, as well as various control mechanisms for the medical system 10 may be housed in the console 20. In addition to providing an exhaust function for the catheter fluid supply, the console 20 may also include pumps, valves, controllers or the like to recover and/or re-circulate fluid, the elongate body 22, and/or the fluid pathways of the medical device 12. A vacuum pump 52 in the console 20 may create a low-pressure environment in at least the fluid recovery conduit 30 so that fluid is drawn into the fluid recovery conduit 30, away from the distal portion 26 and towards the proximal portion 24 of the elongate body 22. The fluid delivery conduit 28 and fluid recovery conduit 30 may be releasably coupled to the fluid reservoir 38 (such as a refrigerant source) and fluid recovery reservoir 50, respectfully, so that the reservoirs 38, 50 may be changed or replaced. The console 20 may include one or more controllers, processors, and/or software modules containing instructions or algorithms to provide for the automated operation and performance of sequences or procedures.

While the medical device 12 may be in fluid communication with a refrigerant source 38 to cryogenically treat selected tissue, it is also contemplated that the medical device 12 may alternatively or additionally include one or more electrically conductive portions or electrodes thereon coupled to a radiofrequency generator or power source as a treatment or diagnostic mechanism.

Figure 4:
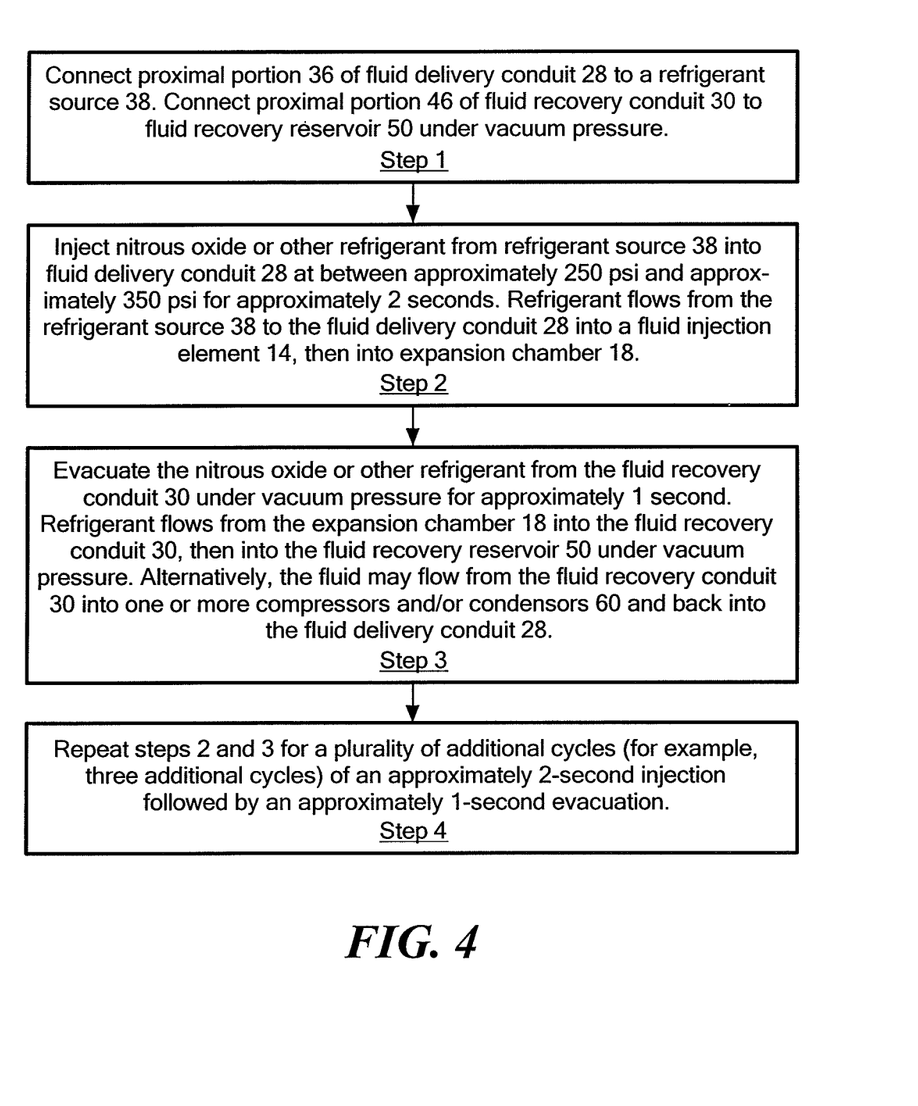
FIG. 4 shows a flow chart of a method for purging a cryoablation system of moisture.

Referring now to FIG. 4, a flow chart of a method for purging a cryoablation system 10 of moisture is shown. The purge process may flush moisture from the fluid flow path and thus prevent any blockage due to ice formation within the system 10 that occurs at the initial refrigerant injection at the beginning of a procedure, for example, a cardiac procedure such as cryablation. In one study, for example, the failure rate associated with obstructed flow at first refrigerant injection was approximately 0.46%. The blockage may occur at any point within a fluid pathway of the system 10, including umbilicals, fluid injection conduit, fluid injection nozzle 14 apertures, and fluid recovery conduit 30.

Although FIG. 4 includes four cycles, the purge process may comprise more than four cycles. In each cycle, nitrous oxide or other refrigerant may be injected from the fluid reservoir 38 (such as a refrigerant source) into the fluid delivery conduit 28 at a high pressure that evacuates or flushes any humidity or moisture within the fluid pathway. For example, the nitrous oxide or other refrigerant may be injected at a pressure of between approximately 250 psi to approximately 350 psi, which is lower than the minimum injection pressure used during a cryoablation procedure.

In the first step of the purge process, the proximal portion 36 of the fluid delivery conduit 28 may be connected to a refrigerant source 38 via one or more umbilicals 58 (which may be part of the fluid delivery and recovery conduits) and/or connecting means 56. Likewise, the proximal portion of the fluid recovery conduit 30 may be connected to a fluid recovery reservoir 50 under vacuum pressure via one or more umbilicals 58 (which may be part of the fluid recovery and delivery conduits) and/or connecting means 56. This may establish a fluid pathway 62 from, generally, the refrigerant source 38, into the fluid delivery conduit 28, through the fluid injection nozzle 14 (or other fluid injection element), into the fluid recovery conduit 30, and into the fluid recovery reservoir 50.

In the second step of the purge process, nitrous oxide or other refrigerant from the fluid reservoir 38 (such as a refrigerant source) may be injected into the fluid delivery conduit 28. The refrigerant may be injected at a pressure of 300 psi for a period of approximately 2 seconds. The refrigerant is injected into the fluid pathway 62 at a lower pressure than the injection pressure used in a cryoablation procedure. As such, the refrigerant flushes moisture or humidity from the fluid pathway 62 and thus prevents ice blockages from forming when refrigerant is later injected at a normal procedure pressure (as a non-limiting example, normal procedure pressure may be between approximately 400 psi and 800 psi). Refrigerant injected into the fluid delivery conduit 28 flows into the fluid injection nozzle 14 (or other fluid injection element) and into the cryoballoon lumen 18.

In the third step of the purge process, the nitrous oxide or other refrigerant may be evacuated from the fluid recovery conduit 30 under vacuum pressure for approximately 1 second. In this step, refrigerant from the cryoballoon lumen 18 may be drawn in to the fluid recovery conduit 30 under vacuum pressure, from where it is collected in a fluid recovery reservoir 50. The recovered fluid may be discarded or it may be compressed and/or conditioned by one or more compressors and/or condensers 60 for reuse in a subsequent cycle.

In the fourth step of the purge process, Steps 2 and 3 are repeated for a plurality of cycles. For example, Steps 2 and 3 may each be performed four times each. At the end of the purging process, the fluid pathway of the system 10 may be clear of moisture, and the system 10 may be ready for performing a medical procedure without the risk of ice blockages occurring at the initial injection of refrigerant. The entire purge process may take far less than one minute. Therefore, the purge process described herein may reduce the delay required by presently known purging processes and may eliminate the delay caused by injection failure due to ice blockages in the flow path of the system 10. Thus, medical procedures such as cryosurgical procedures may be performed quickly and efficiently.

It will be appreciated by persons skilled in the art that the present invention is not limited to what has been particularly shown and described herein above. In addition, unless mention was made above to the contrary, it should be noted that all of the accompanying drawings are not to scale. A variety of modifications and variations are possible in light of the above teachings without departing from the scope and spirit of the invention, which is limited only by the following claims.

What is claimed is:

1. A method of purging a cryotreatment fluid flow path comprising:
   (a) providing a cryotreatment system including a refrigerant source, a fluid delivery conduit in fluid communication with the refrigerant source, a fluid injection element in fluid communication with the fluid delivery conduit, a fluid recovery conduit in fluid communication with the fluid injection element, and a vacuum pump in fluid communication with and providing a low pressure environment within the fluid recovery conduit;
   (b) injecting refrigerant from the refrigerant source into the fluid delivery conduit for two seconds at a preselected injection pressure that is less than a cryoablation minimum injection pressure, the refrigerant flowing from the fluid delivery conduit through the fluid injection element and into the fluid recovery conduit;
   (c) then evacuating refrigerant from the fluid recovery conduit by vacuum pressure generated by the vacuum pump for one second; and
   (d) then injecting refrigerant from the refrigerant source into the fluid delivery conduit at a pressure that is at least the cryoablation minimum injection pressure.

2. The method of claim 1, further comprising repeating steps (b) and (c) for a total of four or more cycles before performing step (d).

3. The method of claim 1, wherein the cryotreatment system further includes an expansion chamber.

4. The method of claim 3, wherein the refrigerant flows from the fluid delivery conduit through the fluid injection element and into the expansion chamber, from which the refrigerant then flows into the fluid recovery conduit.

5. The method of claim 4, wherein the refrigerant from the refrigerant source is compressed refrigerant, the compressed refrigerant expands within the expansion chamber, and the expanded refrigerant is evacuated from the fluid recovery conduit.

6. The method of claim 1, wherein the preselected injection pressure is between 250 psi and 350 psi.

7. The method of claim 6, wherein the preselected injection pressure is 300 psi.

8. The method of claim 7, wherein the refrigerant is nitrous oxide.

9. The method of claim 2, wherein the cryotreatment system further includes a fluid recovery reservoir in fluid communication with the fluid recovery conduit.

10. The method of claim 9, wherein the method further comprises evacuating the refrigerant from the fluid recovery conduit into the fluid recovery reservoir.

11. The method of claim 5, wherein the method further comprises evacuating the expanded refrigerant from the fluid recovery conduit and recompressing the expanded refrigerant.

12. The method of claim 11, wherein the method further comprises directing the recompressed refrigerant to the fluid delivery conduit.

13. The method of claim 5, wherein the cryotreatment system further includes a cryoablation device having an expansion chamber that is in fluid communication with the fluid delivery conduit and the fluid recovery conduit.

14. The method of claim 8, wherein the cryotreatment system further comprises a cryoablation device having an expansion chamber in fluid communication with the fluid delivery conduit and the fluid recovery conduit.

15. The method of claim 14, wherein the cryoablation device is a balloon catheter and the expansion chamber is a balloon lumen, and the fluid injection element is a fluid injection nozzle.

16. The method of claim 8, wherein the cryotreatment system further include a cryoablation balloon catheter including a shaft and a balloon defining a lumen, the fluid injection element being a fluid injection nozzle disposed within the balloon lumen, having a plurality of apertures, and being coiled about at least a portion of the shaft.

17. A method of removing moisture from a cryotreatment fluid flow path comprising:
   (a) providing a cryotreatment system defining a fluid flow path including:
      a fluid delivery conduit in fluid communication with a refrigerant source;
      a cryotreatment device having a balloon defining a lumen;

a fluid injection element in fluid communication with the fluid delivery conduit and being disposed within the balloon lumen;

a fluid recovery conduit in fluid communication with the balloon lumen;

a vacuum pump in fluid communication with and providing a low pressure environment within the fluid flow path; and a compressor in fluid communication with the fluid recovery conduit and the fluid delivery conduit;

(b) injecting compressed refrigerant from the refrigerant source into the fluid delivery conduit at a pressure of between 250 psi and 350 psi for two seconds, the compressed refrigerant flowing from the fluid delivery conduit through the fluid injection element and into the balloon lumen where the compressed refrigerant expands, the expanded refrigerant then flowing into the fluid recovery conduit;

(c) evacuating the expanded refrigerant from the fluid recovery conduit into the fluid recovery conduit by low pressure generated by the vacuum pump for one second;

(d) directing the expanded refrigerant into the compressor and recompressing the expanded refrigerant, the compressor becoming the refrigerant source;

(e) repeating (b) and (c) for a plurality of additional cycles; and (f) then injecting compressed refrigerant from the refrigerant source into the fluid delivery conduit at a pressure of between 400 psi and 800 psi and performing a cryoablation procedure.

18. A method of removing moisture from a cryotreatment fluid flow path comprising:

(a) providing a cryotreatment system defining a fluid flow path including:

a refrigerant source;

a fluid delivery conduit in fluid communication with the refrigerant source;

a cryotreatment device having an elongate body, a balloon defining a lumen and a shaft having at least a portion disposed within the elongate body and at least a portion disposed within the balloon lumen;

a fluid injection element in fluid communication with the fluid delivery conduit and being disposed about at least a portion of the shaft within the balloon lumen;

a fluid recovery conduit in fluid communication with the balloon lumen;

a fluid recovery reservoir in fluid communication with the fluid recovery conduit; and a vacuum pump in fluid communication with and providing a low pressure environment within the fluid recovery reservoir;

(b) injecting refrigerant from the refrigerant source into the fluid delivery conduit at a pressure of between 250 psi and 350 psi for two seconds, the refrigerant flowing from the fluid delivery conduit through the fluid injection element, into the balloon lumen, and then into the fluid recovery conduit;

(c) then evacuating refrigerant from the fluid recovery conduit into the fluid recovery reservoir by vacuum pressure generated by the vacuum pump for one second;

(d) repeating (b) and (c) for three additional cycles; and (e) then injecting refrigerant from the refrigerant source into the fluid delivery conduit at a pressure of between 400 psi and 800 psi to perform cryoablation procedure.

* * * * *